United States Patent [19]
Bergersen

[11] Patent Number: 6,129,084
[45] Date of Patent: Oct. 10, 2000

[54] INTRA-ORAL APPLIANCE FOR THE PREVENTION OF SNORING

[76] Inventor: Earl O. Bergersen, 950 Green Bay Rd., Winnetka, Ill. 60093

[21] Appl. No.: 09/176,778

[22] Filed: Oct. 22, 1998

[51] Int. Cl.[7] .................................................. A61F 5/56
[52] U.S. Cl. ......................... 128/848; 128/859; 128/860; 128/861
[58] Field of Search ................... 128/846, 848, 128/859–862; 433/6, 7

[56] References Cited

U.S. PATENT DOCUMENTS

| | | | |
|---|---|---|---|
| 2,857,909 | 10/1958 | Johnson | 128/136 |
| 4,114,614 | 9/1978 | Kesling | 128/136 |
| 4,898,535 | 2/1990 | Bergersen . | |
| 4,901,737 | 2/1990 | Toone . | |
| 5,003,994 | 4/1991 | Cook . | |
| 5,092,346 | 3/1992 | Hays, et al. . | |
| 5,117,816 | 6/1992 | Shapiro et al. . | |
| 5,277,202 | 1/1994 | Hays . | |
| 5,313,960 | 5/1994 | Tomasi . | |
| 5,316,020 | 5/1994 | Truffer . | |
| 5,365,945 | 11/1994 | Halstrom . | |
| 5,409,017 | 4/1995 | Lowe . | |
| 5,427,117 | 6/1995 | Thornton . | |
| 5,462,066 | 10/1995 | Snyder . | |
| 5,499,633 | 3/1996 | Fenton | 128/848 |
| 5,562,106 | 10/1996 | Heeke et al. . | |
| 5,566,683 | 10/1996 | Thornton . | |
| 5,570,704 | 11/1996 | Buzzard et al. . | |
| 5,611,355 | 3/1997 | Hilsen . | |
| 5,642,737 | 7/1997 | Parks . | |

*Primary Examiner*—Michael A. Brown
*Attorney, Agent, or Firm*—Hill & Simpson

[57] ABSTRACT

An intra-oral appliance is disclosed for repositioning the user's mandible anterior to the user's maxillary teeth thus opening the user's oral and pharyngeal passageway and preventing snoring and sleep apnea. The appliance is two U-shaped plates joined to form a hinge. The upper plate has a labial-buccal wall but no lingual wall, which allows anterior positioning of the tongue. The lower plate has both a labial-buccal wall and a lingual wall. The walls are pliable to reduce pressure on the user's teeth and vary in height and thickness. Lingual tabs are employed to help position the appliance. A method for using the intra-oral appliance is also disclosed.

27 Claims, 1 Drawing Sheet

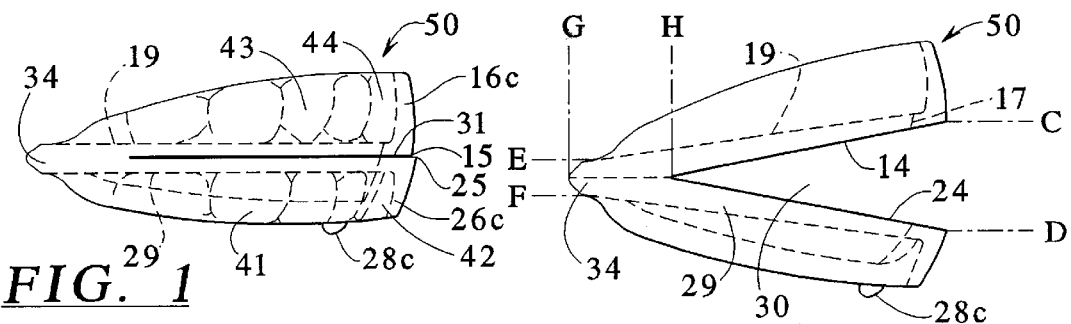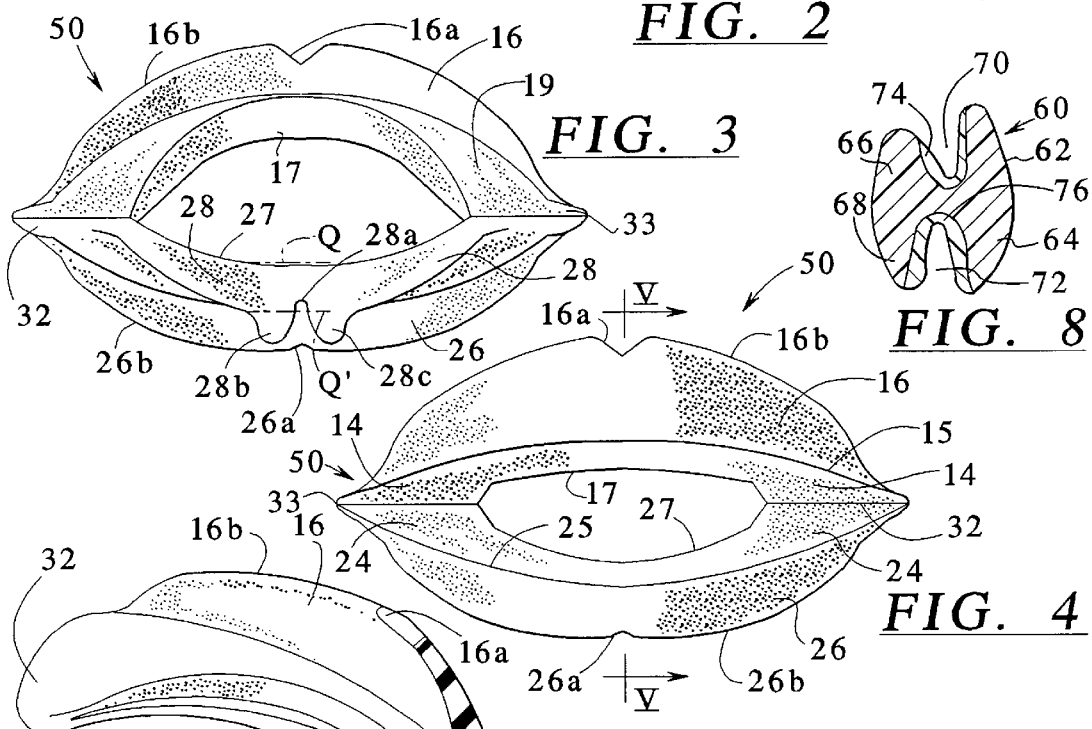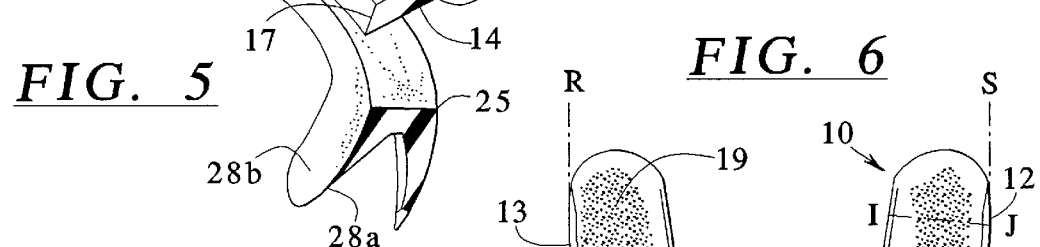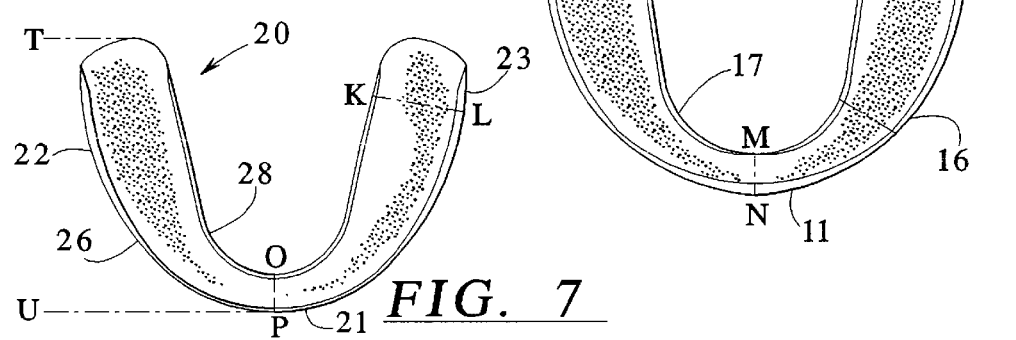

INTRA-ORAL APPLIANCE FOR THE PREVENTION OF SNORING

FIELD OF THE INVENTION

The present invention relates to snoring prevention devices, specifically to an intra-oral appliance for altering the position of the mandible to reduce restriction of the flow of air through the user's oral and pharyngeal passageway. Reduced restriction of the flow of air through the oral and pharyngeal passageway decreases soft tissue vibration which causes snoring. Reduced restriction in the oral and pharyngeal passageway also reduces the likelihood of sleep apnea.

BACKGROUND OF THE INVENTION

Snoring is a common problem among people of all ages. Snoring is caused by the vibration of the soft tissues of the uvula, soft palate, and adjacent structures and may result from the restriction of airflow through the pharyngeal passageway. For the most part, snoring is harmless and presents no real physical threat to the snorer. However, the social consequences of this affliction can result in no end of aggravation and annoyance for both snorers and the spouses, children, friends, and others who have to deal with them on a regular basis. Further, some people suffer a more advanced problem known as sleep apnea Sleep apnea actually causes the sleeper to stop breathing during sleep, resulting in a life threatening situation. Both afflictions can be reduced or prevented by decreasing the restriction of the pharyngeal passageway which may naturally occur during sleep.

Countless methods of dealing with snoring have been tried, using many different avenues of treatment. Various belts, pillows, and harnesses have been developed to position the head and body so that snoring is less likely. Several pharmaceutical methods have been employed, such as the administration of muscle relaxants. Complex signal feedback methods, sleep monitoring and interruption regimens, and even surgical avenues have been pursued. Nasal strips and appliances which attempt to control airflow through the nasal passageway have also been tried. Even within the realm of oral appliances many different approaches have been considered: devices which seal off entirely or in some way regulate the flow of air through the oral passageway; devices to hold the tongue in a specific position or brace the tissues of the mouth in a specific way; or, the arena of the present invention, devices which reposition the mandible to promote airflow through the pharyngeal passageway.

Opening the mouth and anteriorly repositioning the mandible has proven a successful means for preventing snoring. However, the general solution still presents many difficulties in application. In order to reposition the mandible, an oral appliance is placed in the mouth of the user to engage some portion of the maxillary and mandibular structures of the mouth. The oral appliance needs to stay in position in spite of the user's nocturnal movements. The appliance has to be fairly comfortable and easy to wear or users will either stop using it, or lose sleep due to discomfort. The appliance must be either custom fitted or designed in such a way that it does not cause undue pressure on the teeth which could cause pain or even reorient the user's teeth over a prolonged period. Ideally, the appliance should be inexpensive to manufacture and generally adaptable to many different users. Unrestricted airflow through the oral passageway and the ability of the appliance to move with the user's natural articulation would be further positive design features. Previous designs have all fallen short in one way or another in meeting the above proposed design criteria.

One area of prior art designs in mandible repositioning intra-oral appliances are those composed of opposed bite plates or tooth receiving troughs with some sort of connection means to maintain the relative positions of the two plates or troughs. Some of these designs involve an anterior relational connector such as hook and loop plates (U.S. Pat. No. 5,642,737), a screw and threaded plate assembly (U.S. Pat. No. 5,365,945), or a block or tab extending from the upper plate or trough which holds the lower plate forward (U.S. Pat. No. 5,427,117 and U.S. Pat. No. 5,566,683). Other designs employ paired posteriorly mounted connection means such as detachably connectable plates (U.S. Pat. No. 5,611,355) or mutually engaging teeth or ridges (U.S. Pat. No. 5,449,633 and U.S. Pat. No. 5,570,704). Another design connects the anterior portion of the lower plate or trough to the posterior portion of the upper plate or trough via a complex adjustable assembly (U.S. Pat. No. 5,409,017). Still another design involves a separate mounting structure to which the two plates or troughs are attached (U.S. Pat. No. 5,313,960). These designs are all complex multi-part assemblies which may not maintain their position within the user's mouth over a prolonged period and many of them necessarily restrict air flow through the oral cavity. None can articulate with the user's natural movements without the risk of losing the repositioning relationship between the two plates or troughs. Most of the above designs are custom molded to conform to a particular user's teeth.

A second area of prior art designs in mandible repositioning intra-oral appliances are custom molded single piece appliances designed to hold a specific user's oral structures in a particular orientation (U.S. Pat. No. 4,901,737 and U.S. Pat. No. 5,562,106). These rigid structures are expensive due to their professionally customized nature and do not possess any ability to articulate with the user's movements. They are expressly designed to limit any oral movement.

Among the more universal single piece prior art designs in mandible repositioning intra-oral appliances are those which have a single bite plate which is engaged by both the maxillary and mandibular teeth and have extended walls on either or both the lingual and labial-buccal sides of the plate (U.S. Pat. No. 5,316,020 and U.S. Pat. No. 5,462,066). These designs neither articulate with the movements of the user, nor do they allow air to pass easily through the oral passageway.

Another area of prior art designs in mandible repositioning intra-oral appliances involve a single piece appliance with an upper plate or tooth receiving trough and a lower ramp or cam structure for engaging the mandibular teeth and forcing the mandible into an open and anterior position (U.S. Pat. No. 5,003,994, U.S. Pat. No. 5,092,346, U.S. Pat. No. 5,117,816, and U.S. Pat. No. 5,277,202). These designs generally include a breathing aperture between the upper plate or tooth receiving trough and the cam structure. While these designs represent advancement towards an intra-oral device which meets the above design criteria, inventors continue to struggle to optimize sizing, thickness, and wall locations for the upper plate or trough and to perfect a means of positioning the tongue so it does not interfere with the breathing aperture. Further, the above designs, while allowing natural articulation of the mouth for yawning and similar movements, attain this freedom of movement by having the lower ramp or cam structure disengage from the mandibular teeth, thus potentially allowing the device to become reoriented relative to the mandible.

Inventors of intra-oral appliances for the prevention of snoring have noted closely related areas of art such as athletic mouth guards and corrective orthodontic appliances.

I have been most active in the area of corrective orthodontic appliances. I have modified one of my designs for orthodontic appliances to an optimal configuration for the prevention of snoring. My self-opening hinge design for orthodontic appliances allows positioning of the mandible in an open and anterior position, promotes airflow through the oral passageway, and articulates with the user's motions to maintain contact with both the maxillary and mandibular interface (U.S. Pat. No. 4,898,535). I have further modified this design to reduce pressure on the user's teeth, optimize the use of materials, be further adaptable to multiple mouth sizes, and facilitate tongue placement so the tongue does not block airflow through the oral passageway.

SUMMARY OF THE INVENTION

The present invention is an intra-oral appliance for reducing restriction in a user's oral and pharyngeal passageway by opening the mouth and anteriorly repositioning the user's mandible. The appliance is made up of two U-shaped plates. The upper plate engages at least some portion of the user's maxillary teeth and the lower plate engages at least some portion of the user's mandibular teeth. The U-shaped plates have an anterior portion located at the bight of the U-shape and first and second posterior portions located at the ends of the U-shape. The outward facing edges of the plates, which face the user's cheeks and lips when the appliance is in use, are referred to as the labial-buccal edges and the inward facing edges of the plates, which face the user's tongue and inner mouth when the appliance is in use, are referred to as the lingual edges. The width of the plates, as measured from the labial-buccal edge to the lingual edge, may vary along the U-shape and may be substantially wider near the posterior portions and substantially narrower toward the anterior portion.

The anterior portions of the plates define a gap which separates the anterior portions from each other and extends toward the posterior portions of the plates. The posterior portions of the plates are connected to each other to form a first and second hinge portion with the first posterior portion of the upper plate connected to the first posterior portion of the lower plate and second posterior portion of the upper plate connected to the second posterior portion of the lower plate. The hinges allow the appliance to articulate with the user's natural mouth movements, such as yawning or chewing, without having to disengage the upper or lower plate from the user's maxillary or mandibular teeth. Proper positioning of the appliance is more likely to be maintained during sleep because the appliance does not disengage from the user's teeth. The hinge portions may be rigidly formed such that the anterior portions of the plates define a substantial gap therebetween and the gap is maintained even when the user applies pressure to the plates.

The upper plate has an upper labial-buccal wall extending upward from the labial-buccal edge of the plate and extending from the anterior portion of the plate toward the first and second hinge portions. The upper labial-buccal wall engages the front of the user's maxillary teeth and helps position and retain the upper plate in the user's mouth. The upper labial-buccal wall may also serve to strengthen the first and second hinge portions. The upper labial-buccal wall may be substantially thin and pliable in order to further decrease any pressure on the user's maxillary teeth. The upper plate lacks a lingual wall in order to create more space for the user's tongue in an upward and forward position, decrease the materials used in the appliance, and allow the upper plate to accommodate a wider variety of user tooth sizes and configurations. The anterior portion of the lingual edge of the upper plate may be beveled to further accommodate the placement of the tongue.

The lower plate has a lower labial-buccal wall extending downward from the labial-buccal edge of the plate and extending from the anterior portion of the plate toward the first and second hinge portions. The lower labial-buccal wall engages the front of the user's mandibular teeth and helps position and retain the lower plate in the user's mouth. The lower labial-buccal wall may also serve to strengthen the first and second hinge portions. The lower plate also has a lingual wall extending downward from the lingual edge of the plate and extending from the anterior portion of the plate toward the first and second hinge portions. A lower tooth receiving trough is formed between the lingual wall and the labial-buccal wall. The lingual wall engages the back of the user's mandibular teeth and helps position and retain the lower plate in the user's mouth. The lingual wall engages the user's mandibular teeth in such a way that they are positioned anterior to the user's maxillary teeth, thus repositioning the mandible in an anterior direction to open the pharyngeal passageway. The height of the lingual wall may vary along the U-shape and may be substantially greater along the anterior portion of the plate and substantially less toward the posterior portions. The lower labial-buccal wall and the lingual wall may be substantially thin and pliable in order to further decrease any pressure on the user's mandibular teeth. The lingual wall may also have a vertical groove in the middle of the anterior portion in order to accommodate the user's lingual frenum. Further, the appliance may have one or more lingual tabs extending from the lingual wall.

Ideally, the appliance is molded as a single piece from a thermoplastic material and is sized appropriately to fit a common range of mouth sizes. The appliance is designed not to require the use of user or doctor customizable materials such as the low temperature moldable plastics used in many athletic mouth guards and other anti-snoring devices, though it is still possible to use these materials.

As an alternative construction, the device could include a "re-liner" in the form of a lining material formed of a soft acrylic, silicone, PVC or similar rubbery material in the tooth receiving trough of the device. As an example, uncured material can be dispensed into the trough and the user would insert the device into their mouth and close down the teeth to let the material set. This rubbery re-liner will then go in an around the teeth and enable the device to securely engage these teeth. This will increase the ability of the appliance to stay in the mouth at night while the user is sleeping.

Such a construction can also be used with other types of devices for use within the mouth, including tooth straightening positioners and devices to help retain or keep the teeth straight. In such devices typically there are both lower and upper tooth receiving troughs and the material can be used in either one or both troughs. Generally such devices may be used after standard orthodontics treatment is completed or once the teeth are in an acceptable alignment. Thus, a much more tightly fitting retaining device would be provided. Such an arrangement can also be used in mouth guards.

The present invention is also a method of using an intra-oral device. The method includes inserting an intra-oral appliance into the user's mouth which engages at least some portion of the user's maxillary and mandibular teeth. The user's anterior mandibular teeth are repositioned anterior to the user's anterior maxillary teeth. The user is allowed to articulate his mouth naturally for motions such as chewing or yawning without the appliance disengaging from the user's teeth. The user's tongue is positioned to be in contact with the lingual side of the user's anterior maxillary teeth. The combination of these steps enlarges the user's oral and pharyngeal passageway and will prevent snoring and sleep apnea

BRIEF DESCRIPTION OF THE DRAWINGS

FIG. 1 is a side view of the preferred embodiment of the invention held closed by pressure from the user's teeth.

FIG. 2 is a side view of the preferred embodiment in an open position.

FIG. 3 is a rear view of the preferred embodiment in an open position.

FIG. 4 is a front view of the preferred embodiment in an open position.

FIG. 5 is a view showing the cross-section of the preferred embodiment along the midline V of FIG. 4.

FIG. 6 is an overhead view of the upper plate of the preferred embodiment.

FIG. 7 is an underside view of the lower plate of the preferred embodiment.

FIG. 8 is a cross sectional view of an alternative embodiment of the invention.

DETAILED DESCRIPTION OF THE PREFERRED EMBODIMENT

The preferred embodiment of the invention is an intra-oral appliance for reducing restriction in the oral and pharyngeal passageway of a user as shown in FIGS. 1–7. The appliance 50 comprises a U-shaped upper plate 10 as shown in FIG. 6. Upper plate 10 has an anterior portion 11 at the bight of the U-shape and a first posterior portion 12 and a second posterior portion 13 at the ends of the U-shape. Upper plate 10 also has an outward facing labial-buccal edge 15 which faces the lips and cheeks of the user and an inward facing lingual edge 17 which faces the tongue and inner mouth of the user. Upper plate 10 has a width measured between labial-buccal edge 15 and lingual edge 17 which varies along the U-shape. The width is substantially greater proximate first posterior portion 12 and second posterior portion 13 compared to the width at anterior portion 11. The posterior width I-J is approximately 15 mm, measured between labial-buccal edge 15 at first posterior portion 12 (J) and lingual edge 17 at first posterior portion 12 (I). The same measurement can be made at second posterior portion 13. The anterior width M-N is approximately 8 mm, measured between labial-buccal edge 15 at anterior portion 11 (N) and lingual edge 17 at anterior portion 11 (M).

The appliance 50 further comprises a U-shaped lower plate 20 as shown in FIG. 7. Lower plate 20 has an anterior portion 21 at the bight of the U-shape and a first posterior portion 22 and a second posterior portion 23 at the ends of the U-shape. Lower plate 20 also has an outward facing labial-buccal edge 25 which faces the lips and cheeks of the user and an inward facing lingual edge 27 which faces the tongue and inner mouth of the user. Lower plate 20 has a width measured between labial-buccal edge 25 and lingual edge 27 which varies along the U-shape. The width is substantially greater proximate first posterior portion 22 and second posterior portion 23 compared to the width at anterior portion 21. The posterior width K-L is approximately 15 mm, measured between labial-buccal edge 25 at first posterior portion 22 (L) and lingual edge 27 at first posterior portion 22 (K). The same measurement can be made at second posterior portion 23 The anterior width O-P is approximately 8 mm, measured between labial-buccal edge 25 at anterior portion 21 (P) and lingual edge 27 at anterior portion 21 (O).

Anterior portion 21 and anterior portion 11 are separated at contact plane 31 when the device is held closed by pressure from the user's teeth (FIG. 1). Anterior portion 21 and anterior portion 11 are separated by gap 30 between lower surface 14 of the upper plate 10 and upper surface 24 of the lower plate 20 when the appliance is in an open position as in FIG. 2.

First posterior portion 12 and first posterior portion 22 are joined to form first hinge portion 32. Second posterior portion 13 and second posterior portion 23 are joined to form second hinge portion 33. First hinge portion 32 and second hinge portion 33 collectively form hinge 34. The appliance is in an open position when not in use or when the user's jaw is sufficiently relaxed to allow self-opening hinge 34 to maintain the open position. Hinge 34 may be sufficiently rigid to maintain a substantial gap 30 in an open position even when the user applies considerable force (i.e. users who clench their teeth while sleeping). The vertical distance C-D between labial-buccal edge 15 of upper plate 10 at anterior portion 11 (C) and labial-buccal edge 25 of lower plate 20 at anterior portion 21 (D), when the appliance has no pressure applied to either plate, is approximately 28 mm. Hinge 34 has a vertical thickness E-F of approximately 3 mm, measured between the horizontal teeth engaging surface 19 at second hinge portion 33 (E) and the horizontal teeth engaging surface 29 at second hinge portion 33 (F). Hinge 34 has a length G-H of approximately 13 mm, measured between the posterior most end of second hinge portion 33 (G) and the point where lower surface 14 and upper surface 24 end and second hinge portion 33 is formed (H). The same measurements of hinge 34 can be made at hinge portion 32.

Upper plate 10 has an upper labial-buccal wall 16 extending upward from labial-buccal edge 15. Upper labial-buccal wall 16 extends laterally from anterior portion 11 to adjacent first hinge portion 32 and laterally in the opposite direction to second hinge portion 33. Upper labial-buccal wall 16 has a height which varies along the U-shape, measured from labial-buccal edge 15 to upper edge 16b of 12 mm at the midline 16a, 11 at the canine area (16b) and 8 mm at molar area (H). Upper edge 16b may define a vertical groove 16a in upper labial-buccal wall 16 at the midline of anterior portion 11. The upper labial-buccal wall 16 is substantially thin and pliable to place minimal pressure on the user's maxillary teeth 43. The thickness of upper labial-buccal wall 16 varies along the U-shape from substantially thicker proximate first posterior portion 12 of 15 mm, second posterior portion 13, and anterior portion 11 to substantially thinner of 8 mm in the medial portions connecting the anterior and posterior portions. The thickness of upper labial-buccal wall 16 varies in a range of 8–15 mm.

Upper plate 10 lacks a lingual wall extending from lingual edge 17. The lingual edge 17 at anterior portion 11 is beveled toward teeth engaging surface 19, whereby a user's tongue may be accommodated in an anterior position and positioned in contact with the lingual surface of the user's maxillary teeth 43.

Lower plate 20 has a lower labial-buccal wall 26 extending downward from labial-buccal edge 25. Lower labial-buccal wall 26 extends laterally from anterior portion 21 to adjacent first hinge portion 32 and laterally in the opposite direction to adjacent second hinge portion 33. Lower labial-buccal wall 26 has a height which varies along the U-shape, measured from labial-buccal edge 25 to lower edge 26b of 11 mm. Lower edge 26b may define a vertical groove 26a in lower labial-buccal wall 26 at the midline of anterior portion 21. Lower labial-buccal wall 26 is sufficiently thin and pliable to place minimal pressure on the user's mandibular teeth 41. The thickness of lower labial-buccal wall 26 varies along the U-shape from substantially thicker proximate first posterior portion 22 and second posterior portion 23 and substantially thinner proximate anterior portion 21. The thickness of lower labial-buccal wall 26 varies in a range of 13 mm. The thickness of upper labial-buccal wall 16 at anterior portion 11 (16c) is greater than the thickness of lower labial-buccal wall 26 at anterior portion 21 (26c). The difference between the thickness at the portion 16c and the portion 26c is approximately 1 mm.

Lower plate 20 has a lingual wall 28 extending downward from lingual edge 27. Lingual wall 28 extends laterally from anterior portion 21 to adjacent first hinge portion 32 and laterally in the opposite direction to adjacent second hinge portion 33. Lingual wall 28 has a height which varies in height along the U-shape. Lingual wall 28 has a height Q-Q' (FIG. 3) of approximately 5 mm measured between lingual edge 27 proximate anterior portion 21 (Q) and lower edge 28d proximate anterior portion 21 (Q'). The height of lingual wall 28 diminishes to 0 mm proximate first hinge portion 32 and second hinge portion 33. Lower edge 28d defines a vertical groove 28a in lingual wall 28 proximate the midline of lingual wall 28 at anterior portion 21 for accommodating the user's lingual frenum. Lingual wall 28 also has one or more lower lingual tabs (lingual tab 28b and lingual tab 28c) extending downward from lower edge 28d to help hold the appliance in place against the lingual surface of the user's mandibular teeth 41. The appliance 50 has two lingual tabs, lingual tab 28b disposed on one side of the midline of anterior portion 21 and lingual tab 28c disposed on the other side of the midline of anterior portion 21. The total length of lingual tabs 28b and 28c is 8 mm, measured from lingual edge 27. Lingual wall 28 should be sufficiently thin and pliable to place minimal pressure on the user's mandibular teeth 41.

Anterior portion 11 and anterior portion 21 are positioned such that the user's mandibular teeth 41, specifically the forward-most lower incisors 42, are positioned anterior to the user's maxillary teeth 43, specifically the forward-most upper incisors 44. The appliance 50 should position the user's mandibular teeth 41 approximately 2 mm forward of an end to end position with the user's maxillary teeth 43. The labial-buccal edge 15 of upper plate 10 at anterior portion 11 is positioned equal to the labial-buccal edge 25 of lower plate 20 at anterior position 21. As described above, the greater thickness of the labial-buccal wall 16 of upper plate 10 at anterior portion 11 accounts for the remaining 2 mm of the 2 mm difference in forward position.

The external dimensions of the appliance are a width R-S of approximately 60 mm measured between the labial buccal side of first hinge portion 32 (S) and the labial-buccal side of second hinge portion 33 (R) and a length T-U of approximately 45 mm measured between the distal end of lower plate 20 (T) and the front end of lower plate 20 (U).

The appliance may be made of a thermoplastic or similar material known in the art of intra-oral devices. Rigid materials may be used, but at the loss of at least some of the articulation which is an important benefit of appliance 50.

Appliance 50 is used by inserting the appliance into a user's mouth and engaging at least some portion of the user's maxillary and mandibular teeth. The appliance repositions the user's anterior mandibular teeth anterior to the user's anterior maxillary teeth. The user's mouth is allowed to articulate naturally without the appliance disengaging from the user's maxillary and mandibular teeth. The tongue is positioned in contact with the lingual side of the user's anterior maxillary teeth and the user's oral and pharyngeal passageway is enlarged.

FIG. 8 shows an alternative embodiment of the present invention in which there is illustrated a device 60 which could be any one of a tooth retainer and positioner, a tooth moving device, a tooth straightening device, a mouth guard or an anti-snoring device. This device is shown in cross section form taken generally along the mid line or bight region of the device. What is shown is an upper labial-buccal wall 62 and a lower labial-buccal wall 64 as well an upper lingual wall 66 and a lower lingual wall 68. The upper labial-buccal and lingual walls form an upper receiving trough 70 therebetween and the lower labial-buccal wall 64 and lingual wall 68 form a lower tooth receiving trough 72 therebetween. As described above, if the device is used as an anti-snoring device, the upper lingual wall 66 would not be present.

Applied to the upper trough 70 is a "re-liner" 74 and applied to the lower trough 72 is a re-liner 76. The re-liner is a lining material formed of a soft material such as acrylic, silicone, PVC or similar rubbery, resilient material which is deposited into the upper 70 and/or lower 72 trough. The user of the device places the device into their mouth and closes down the teeth into the troughs 70, 72 to engage into the re-liner material until the re-liner material sets. This re-liner material will then flow in and around the teeth and will enable the device 60 to securely engage the teeth. This re-liner material will increase the ability of the device to stay in the user's mouth at night while the user is sleeping and will increase dramatically the ability of the device to hold teeth exactly in place if the device is used following a tooth straightening procedure. If the device is used after a tooth straightening procedure and it is suspected that only the lower or the upper arch will have a tendency to relapse, then only the upper or lower trough will need to have the re-liner material applied thereto. In some devices there may be only an upper or lower trough, depending on the configuration and use of the device, so in that case, obviously, the re-liner material would be applied only to the single trough.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. An intra-oral appliance for reducing restriction in an oral and pharyngeal passageway, comprising:

a U-shaped upper plate for engaging at least some portion of a user's maxillary teeth, said upper plate having an anterior portion located at a bight of the U-shape, first and second posterior portions located at ends of the U-shape, an outward facing labial-buccal edge, and an inward facing lingual edge;

a U-shaped lower plate for engaging at least some portion of a user's mandibular teeth, said lower plate having an anterior portion located at a bight of the U-shape, first and second posterior portions located at ends of the U-shape, an outward facing labial-buccal edge, and an inward facing lingual edge;

said anterior portion of said upper plate separated from said anterior portion of said lower plate;

first and second hinge portions connecting said first posterior portion of said upper plate to said first posterior portion of said lower plate and connecting said second posterior portion of said upper plate to said second posterior portion of said lower plate;

said upper plate having an upper labial-buccal wall extending upward from said labial-buccal edge of said upper plate, said upper labial-buccal wall extending from said anterior portion of said upper plate to adjacent the first and second hinge portions;

said upper plate lacking an upper lingual wall extending upward from said lingual edge such that a user's tongue may be accommodated in an anterior position and positioned in contact with the lingual surface of the user's maxillary teeth;

said lower plate having a lower labial-buccal wall extending downward from said labial-buccal edge of said lower plate, said lower labial-buccal wall extending from said anterior portion of said lower plate to adjacent the first and second hinge portions;

said lower plate further having a lingual wall extending downward from said lingual edge of said lower plate, said lingual wall extending from said anterior portion of said lower plate toward the first and second hinge portions;

said anterior portion of said upper plate and said anterior portion of said lower plate positioned such that a user's mandibular incisors are positioned anterior to a user's maxillary incisors.

2. The intra-oral appliance of claim 1, wherein said first and second hinge portions are rigidly formed such that said anterior portion of said upper plate and said anterior portion of said lower plate define a substantial gap therebetween.

3. The intra-oral appliance of claim 2, wherein the substantial gap defined by said anterior portion of said upper plate and said anterior portion of said lower plate has a vertical dimension of approximately 28 mm.

4. The intra-oral appliance of claim 1, wherein said first and second hinge portions each have a vertical thickness of approximately 3 mm and said first and second hinge portions each have a length of approximately 13 mm.

5. The intra-oral appliance of claim 1, wherein said anterior portion of said upper plate and said anterior portion of said lower plate are positioned such that a user's mandibular incisors are positioned anterior to a user's maxillary incisors by approximately 2 mm.

6. The intra-oral appliance of claim 1, wherein said intra-oral appliance is made of a thermoplastic material.

7. The intra-oral appliance of claim 1, wherein said upper plate and said lower plate each have a width measured from said labial-buccal edge to said lingual edge, said width varying between a substantially greater width proximate said first and second posterior portions to a substantially lesser width proximate said anterior portion.

8. The intra-oral appliance of claim 7, wherein said width of said upper plate varies between approximately 15 mm proximate said first and second posterior portions and approximately 8 mm proximate said anterior portion.

9. The intra-oral appliance of claim 7, wherein said width of said lower plate varies between approximately 15 mm proximate said first and second posterior portions and approximately 8 mm proximate said anterior portion.

10. The intra-oral appliance of claim 1, wherein said lingual edge of said anterior portion of said upper plate is substantially beveled toward a teeth engaging surface of said upper plate whereby a user's tongue may be accommodated in an anterior position.

11. The intra-oral appliance of claim 1, wherein said lingual wall of said lower plate defines a vertical groove in a middle portion of said anterior portion whereby a user's lingual frenum may be accommodated.

12. The intra-oral appliance of claim 1, wherein said intra-oral appliance further comprises one or more lower lingual tabs extending from said lingual wall of said lower plate.

13. The intra-oral appliance of claim 1, wherein said lingual wall of said lower plate has a height, said lingual wall varying between a substantially greater height proximate said anterior portion and a substantially lesser height proximate said first and second posterior portions.

14. The intra-oral appliance of claim 13, wherein said height of said lingual wall of said lower plate is approximately 5 mm adjacent said anterior portion of said lower plate and diminishes to approximately 0 mm toward said first and second posterior portions.

15. The intra-oral appliance of claim 1, wherein a thickness of the anterior portion of said upper labial-buccal wall is greater than a thickness of the anterior portion of said lower labial-buccal wall.

16. The intra-oral appliance of claim 1, wherein said upper labial-buccal wall and said lower labial-buccal wall are each substantially thin and pliable whereby said intra-oral appliance applies substantially little pressure on a user's maxillary teeth.

17. The intra-oral appliance of claim 16, wherein a thickness of said lower labial-buccal wall varies between a substantially greater thickness proximate said first and second posterior portions and a substantially lesser thickness proximate said anterior portion.

18. The intra-oral appliance of claim 17, wherein said thickness of said lower labial-buccal wall each vary within a range of 1–3 mm.

19. The intra-oral appliance of claim 1, wherein said labial-buccal edge of said anterior portion of said upper labial-buccal wall is positioned posterior of said labial-buccal edge of said anterior portion of said lower labial-buccal wall.

20. The intra-oral appliance of claim 1, wherein said intra-oral appliance has a width of approximately 60 mm measured between the labial-buccal edge of the first posterior portion and the labial-buccal edge of the second posterior portion and a length of approximately 45 mm measured between a distal end and a front end of approximately 45 mm.

21. An intra-oral appliance according to claim 1, wherein a soft, resilient re-liner material is secured to said tooth engaging plate to closely engage the user's teeth in said appliance.

22. An intra-oral appliance according to claim 21, wherein said re-liner material is secured to both plates.

23. 24. An intra-oral appliance according to claim 21, wherein said re-liner material is secured to only one of said plates.

24. An intra-oral appliance according to claim 21, wherein said appliance is an anti-snoring device.

25. An intra-oral appliance according to claim 21, wherein said appliance is an orthodontic retaining device to be used after a tooth straightening procedure.

26. An intra-oral appliance according to claim 21, wherein said re-liner material is formed of a material selected from the group consisting of acrylic, silicone and PVC.

27. A method for preventing snoring and sleep apnea comprising the steps of:

inserting an intra-oral appliance into a user's mouth;
engaging at least some portion of the user's maxillary and mandibular teeth with said intra-oral appliance;
repositioning the user's anterior mandibular teeth anterior to the user's anterior maxillary teeth;
allowing the user's mouth to articulate naturally without said intra-oral appliance disengaging from the user's maxillary and mandibular teeth;
positioning the user's tongue in contact with the lingual side of user's anterior maxillary teeth; and
enlarging the user's oral and pharyngeal passageway.

\* \* \* \* \*